Figure 2A:
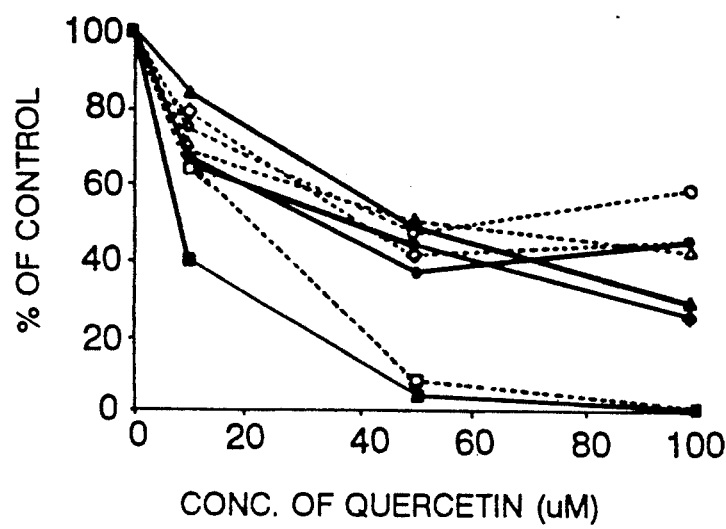

United States Patent [19]

Edgar et al.

[11] Patent Number: 5,229,116

[45] Date of Patent: Jul. 20, 1993

[54] ADMINISTRATION OF PHARMACEUTICAL AGENTS

[76] Inventors: Boo E. Edgar, S-431 83 Molndal, Sweden; David G. Bailey, Department of Medicine, Victoria Hospital, London, Ontario, Canada, N6A 4G5

[21] Appl. No.: 659,495

[22] Filed: Nov. 28, 1990

[30] Foreign Application Priority Data

Nov. 28, 1989 [GB] United Kingdom ............... 8926715

[51] Int. Cl.$^5$ .................... A61K 35/78; A61K 31/44; A61K 31/35
[52] U.S. Cl. ................... 424/195.1; 514/356; 514/456
[58] Field of Search .............. 514/456, 356; 424/195.1

[56] References Cited

U.S. PATENT DOCUMENTS

| | | | |
|---|---|---|---|
| 3,352,754 | 11/1967 | Gazave | 514/456 |
| 4,707,360 | 11/1987 | Brasey | 514/456 |
| 4,885,305 | 12/1989 | Kiechel et al. | 514/356 |

Primary Examiner—Frederick E. Waddell
Assistant Examiner—Raymond J. Henley, III
Attorney, Agent, or Firm—Nixon & Vanderhye

[57] ABSTRACT

The bioavailability of pharmaceutical agents susceptible to oxidation of cytochrome P-450, particularly antihypertensive dihydropyridines such as felodopine or nifedipine can be increased by administering, before, during or after the administration of the pharmaceutical agent, a flavonoid in the aglycone or glycoside form. This conjoint administration has the effect of prolonging the bioavailability of and so reducing the amount of pharmaceutical agent that needs to be administered. Grapefruit juice has been found to be a suitable source of the flavonoid.

7 Claims, 2 Drawing Sheets

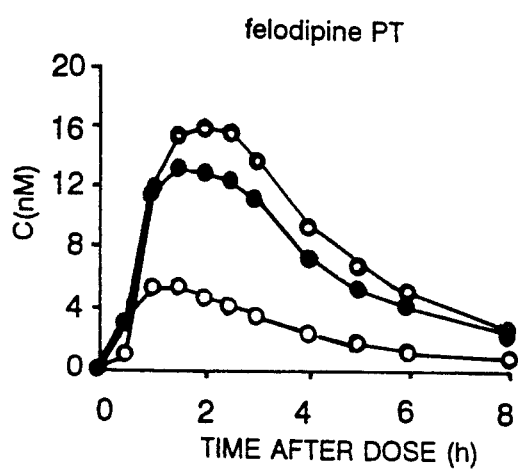
FIG I(A)
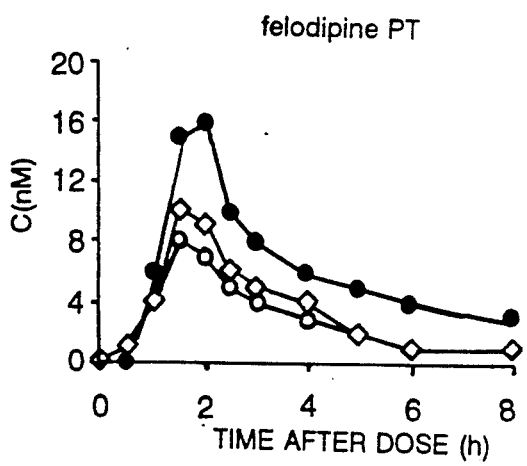
FIG I(B)
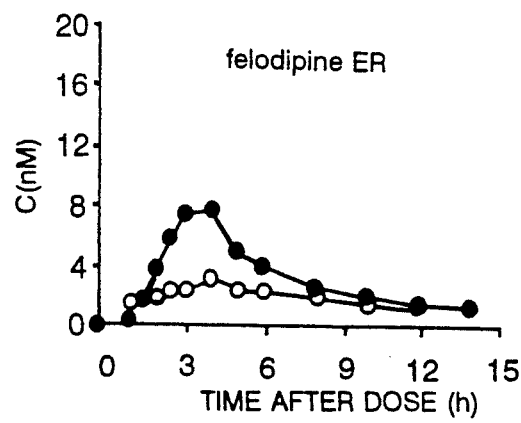
FIG I(C)
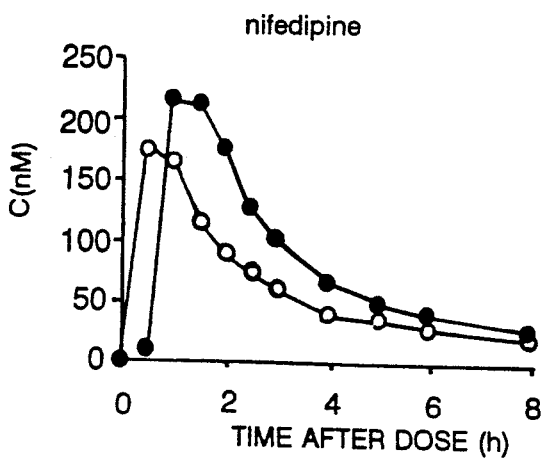
FIG I(D)
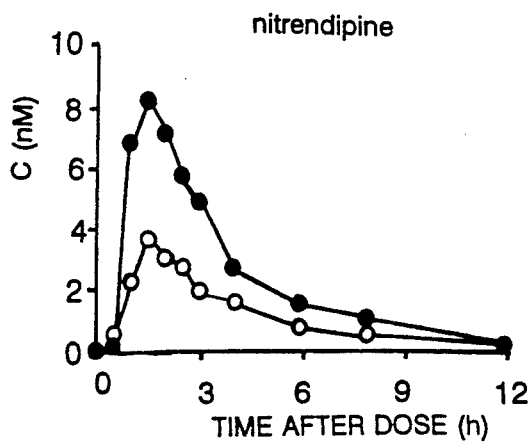
FIG I(E)

ADMINISTRATION OF PHARMACEUTICAL AGENTS

This invention relates to improvements in the administration of pharmaceutical agents, in particular those agents whose bioavailability is lowered through oxidation by cytochrome P-450.

Pharmaceutical agents which are oxidised by cytochrome P-450 include anti-hypertensive agents of the dihydropyridine type, cyclosporins, and steroids, e.g. cortisone.

The clinical use of various dihydropyridine antihypertensive agents such as felodipine, nisedipine, nitredipine etc., is now well established. The dihydropyridine anti-hypertensive agents are customarily administered by the oral route and various types of formulations for oral administration have been proposed in the past with the objective of maintaining a sufficiently high concentration of the dihydropyridine in the bloodstream of the patient.

The dihydropyridines are generally well resorbed from the intestinal tract into the bloodstream of the patients. However, they are rapidly oxidised at the first passage through the liver by the oxidising enzyme system cytochrome P-450, thereby reducing the concentration of the dihydropyridine in the bloodstream of the patient although the dihydropyridine initially was well resorbed from the gastrointestinal tract. Thus the oxidation causes a low bioavailability of the administered dihydropyridine. This implies that the compounds themselves are often well resorbed from the gastrointestinal tract but rapidly metabolised in the liver to inactive metabolites.

We have now discovered that certain flavonoids have the ability of inhibiting cytochrome P-450 activity in vivo and that if such flavonoids are used in combination with pharmaceutical agent susceptible to oxidation, cytochrome P-450, the therapy can become more effective in the sense that the bioavailability of the active ingredient can be increased.

In one aspect, the present invention provides a two-component pack comprising, as a first component, a pharmaceutical agent susceptible to oxidation by cytochrome P-450 and as a second component, a flavonoid of the general formula:

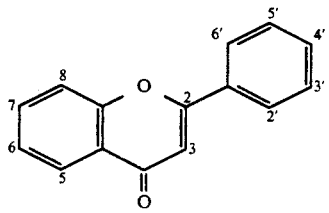

I wherein one or more, for example two to six, of the ring carbons in positions 2, 3, 5, 7, 2', 3', 4' are substituted by hydroxy residues, or the 4' position is optionally substituted by a methoxy residue, the flavonoid being in the form of the aglycone or glycoside and being for administration simultaneously with or shortly before or after administration of the pharmaceutical agent.

In a further aspect, the present invention provides a pharmaceutical composition comprising a pharmaceutical agent as defined above, a flavonoid of the general formula I as defined above and a pharmaceutically acceptable carrier or diluent.

In a still further aspect, the present invention provides a pharmaceutical agent as defined above for use in association with a flavonoid of the general formula I as defined above in a method of therapy practised on the human or animal body.

In accordance with a still further aspect of the present invention, there is provided a method for increasing the bioavailability of a pharmaceutical agent which comprises administering to a patient in need to therapy an effective amount of the said agent as defined above and, simultaneously with or before or after administration of the pharmaceutical agent, administering to the patient an amount of a flavonoid of the general formula I as defined above such that the concentration of the pharmaceutical agent in the serum of the patient is increased compared to the concentration when the flavonoid is not administered.

Pharmaceutical agents of the dihydropyridine type which are suitable for use in the present invention correspond to compounds of the general formula II:

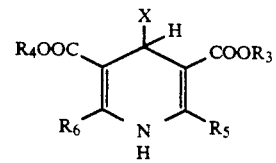

II where X is an optionally substituted phenyl group, or a group

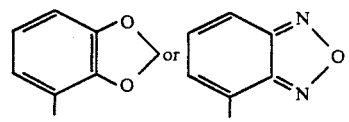

$R_4$ is a group —Y—Z, where Y is a straight or branch chained $C_{1-4}$ alkylene group and Z is either hydrogen, $C_{1-4}$ alkoxy or a group —$ONO_2$, $R_5$ is a straight or branched chain $C_{1-4}$ alkyl, aminoalkyl or carbamylalkyl group, or a cyano group, $R_6$ is a straight or branch chain $C_{1-4}$ alkyl group, and $R_3$ is as defined for $R_4$ or a cyclic phosphate ester, or a branched aza alkyl group wherein the nitrogen atom is at the, or one of the branch points.

Preferred substituents on the phenyl group X are selected from one or more chlorine or fluorine atoms, a nitro group and a group —CH=$CHCOOC_3H_9$.

Preferred aza alkyl groups for $R_3$ are selected from:

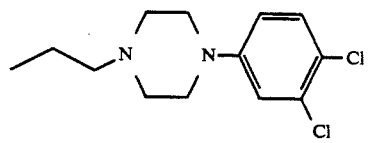

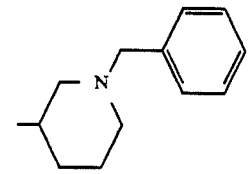

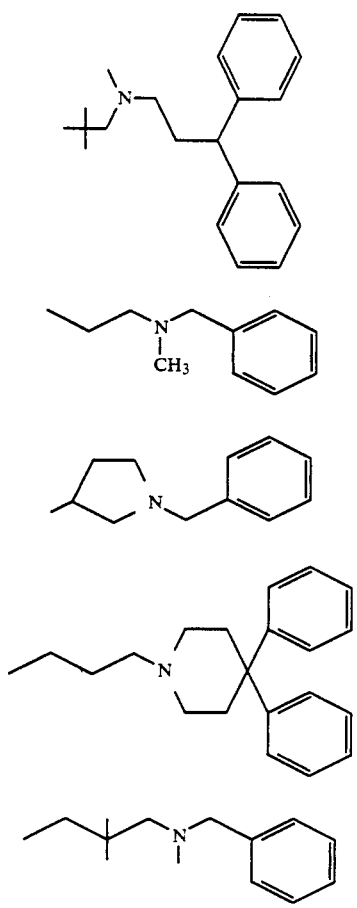

Particularly preferred dihydropyridines are felodopine (X=2-Cl, 3-Cl phenyl, $R_3$=ethyl, $R_4$, $R_5$, $R_6$=methyl) and nifedipine (X=2-$NO_2$ phenyl, $R_3$, $R_4$, $R_5$, $R_6$=methyl).

Flavonoids of interest for use in the invention, and their glycosides are shown in Table I. Quercetin-glycoside (Rutin), Kaempferol-glucoside and Naringenin-glucoside (Naringin) are of particular interest.

The amount of flavonoid which may be prepared for administration as a single dose will vary and will ultimately be determined by the physician. However, in general 100 mg to 1000 mg of the flavonoid compound will be administered in a single dose, e.g. 150 mg.

The amount of the pharmaceutical agent suitable for administration will be in accordance with standard clinical practice. However, since the effect of the flavonoids is to increase the bioavailability of the agents, the dose will be less than the dose administered in the absence of flavonoid. For example, from 1 mg to 50 mg of dihydropyridine may be administered depending upon factors including the potency of the particular dihydropyridine selected. A typical dose of felodipine is 1 mg to 10 mg, e.g. 5 mg. When used in accordance with the present invention, this may be reduced to about 1 mg to 5 mg.

TABLE I

| Aglycone (Flavone as formula) | Substituents on Flavone | Glycoside Flavone + in sugar residues |
|---|---|---|
| Apigenin | 4′,5,7-Trihydroxy- | Apigetin, Apiin |
| Chrysin | 5,7-Dihydroxy- | Toringin |
| Fisetin | 3,3′,4′,7-Tetrahydroxy- | |
| Flavanone | 2,3-Dihydroxy- | |
| Galangin | 3,5,7-Trihydroxy- | |
| Hesperetin | 3′,5,7-Trihydroxy-4′-methoxy | Hesperidin |
| Kaempferol | 3,4′,5,7-Tetrahydroxy- | Kaempferitin, Robinin, Astragalin |
| Morin | 2′,3′,4′,5,7-Pentahydroxy- | |
| Myricetin | 3,3′,4′,5′,7-Hexahydroxy- | Myricitin |
| Naringenin | 4′,5,7-Trihydroxy- | Naringin |
| Quercetin | 3,3′,4′,5,7-Pentahydroxy | Hyperin, Quercitrin, Quercimeritrin, Rutin, Isoquercitrin |

The flavonoids according to the invention may be administered separately or together with the pharmaceutical agents according to the invention. A preferred method of administration is as a single dose in which the pharmaceutical agent and flavonoid is combined. However, a combination of one preparation of the pharmaceutical agent and a separate preparation of the flavonoid may also be used. The separate doses may be presented in a single package or the flavonoids may be presented separately in a form suitable for use as an agent for increasing the bioavailability of drugs which are metabolised by cytochrome P-450.

The flavonoids and pharmaceutical agents may be administered to a patient by any suitable route known in the art. Other customary methods of administration e.g. parenteral, are not excluded, however. The flavonoids and pharmaceutical agents may be formulated conventionally according to the selected route of administration, e.g. into liquid, tablet or capsule form for oral administration, the dosage unit containing the flavonoid and the pharmaceutical agent either together or separately. When the flavonoid and pharmaceutical agent are administered separately, it is convenient to administer them by the same route and when the pharmaceutical agent is a dihydropyridine, the preferred route for this and the flavonoid is oral.

The following Examples are given to illustrate the invention.

EXAMPLE 1

Five in vitro studies were performed to study the effects of the metabolism of dihydropyridines in the presence of flavonoids. Hypertensive patients and healthy volunteers were given commercially available formulations of dihydropyridines in the morning after an overnight fast. The tablets were taken either with water, orange juice, or, as a source of flavonoids, 200 ml grapefruit juice. This contains about 150 mg of flavonoids, either as aglycones or glycosides.

The protocols for the five studies are shown on Table 2.

TABLE 2

| | | Performed in vivo studies. | | |
|---|---|---|---|---|
| Study | Substance | n | Dose/formulation | Comments |
| 1 | Felodipine | 9* | plain tablets | grapefruit juice different strengths |
| 2 | " | 6 | plain tablets | grapefruit juice orange juice |

TABLE 2-continued

| | | Performed in vivo studies. | | |
|---|---|---|---|---|
| Study | Substance | n | Dose/formulation | Comments |
| 3 | " | 9* | extended release (ER) tablets | grapefruit juice |
| 4 | Nifedipine | 6 | 10 mg capsules | grapefruit juice |
| 5 | Nitredipine | 3 | 10 mg tablets | grapefruit juice |

*Seven of these are the same subject

Blood samples for the analysis of the dihydropyridine and the first metabolite were drawn before and at frequent intervals after dose via an indwelling antecubital cannula. Samples were centrifuged and the plasma frozen ($-20°$ C.) until analysis.

Felodipine, nifedipine and their dehydrometabolites analysed using a gaschromatographic (GC) method, with a less than 15% (CV) down to 102 nM (Ahnoff, M. J. Pharmaceut. Biomed. Analysis 2, 519 (1984)). Nitrendipine an its metabolite were analysed using the similar GC method of Soons but with less than 15% down to 0.2 nM. The plasma concentrations of the various dihydropyridines as a function of time in the above studies are shown in FIG. 1.

The maximum plasma concentration, $C_{max}$, and the corresponding time to reach peak concentration, $t_{max}$, were recorded from the individual plasma concentration time curves of the dihydropyridine and its first metabolite. The area from zero to infinity was calculated adding the residual area to the area from zero to last determinable plasma concentration value by using the slope of the log plasma concentration time curve in the 3 to 8 hour interval after dose. The results shown in Table 3 indicate an increase in $C_{max}$ of the dihydropyridines when they are administered with a source of flavonoids i.e. grapefruit juice.

TABLE 3

Mean pharmacokinetic characters of felodipine, nifedipine and nitrendipine given with or without fruit juice.

| | $C_{max}$ (nM) | $t_{max}$ (n) | AUC (nM = h) |
|---|---|---|---|
| Felodipine plain tablets (healthy subjects, n = 9) | | | |
| water | 6.6 ± 3.6 | 1.3 ± 0.6 | 22.8 ± 10.6 |
| grapefruit juice | 16.3 ± 7.1 | 2.1 ± 0.9 | 65.0 ± 26.3 |
| (patients, n = 6) | | | |
| water | 13.2 ± 5.0 | 1.1 ± 0.5 | 48.4 ± 23.7 |
| grapefruit juice | 28.7 ± 7.6 | 2.1 ± 0.5 | 121.2 ± 45.0 |
| orange juice | 16.4 ± 7.8 | 1.9 ± 0.1 | 51.4 ± 22.2 |
| ER tablets (healthy subjects, n = 9) | | | |
| water | 3.4 ± 1.6 | 3.4 ± 0.9 | 27.4 ± 12.3 |
| grapefruit juice | 8.9 ± 3.3 | 3.2 ± 0.8 | 47.8 ± 15.7 |
| Nifedipine (healthy subjects, n = 6) | | | |
| water | 222 ± 54 | 0.8 ± 0.1 | 464 ± 92 |
| grapefruit juice | 250 ± 42 | 1.2 ± 0.1 | 627 ± 152 |
| Nitrendipine (healthy subjects, n = 3) | | | |
| water | 3.7 ± 1.8 | 1.5 ± 0.0 | 15.1 ± 5.8 |
| grapefruit juice | 8.9 ± 4.8 | 1.3 ± 0.5 | 35.0 ± 19.5 |

EXAMPLE 2

In vivo studies

Preparation of microsomes from 4 human livers (2 male and 2 female), supplied by Huddinge Hospital, Sweden, was done according to the method of Emster et al. The method of Lowry et al was used to determine the protein concentration. Two of the flavonoids in grapefruit juice, kaempferol and quercetin, have been used to study the inhibition of R/S felopdipine metabolism in human liver microsomes.

The (R) and (S) entantiomer of felodipine were each incubated at a final concentration of 1 $\mu$M. The in vitro system (water suspension) contained liver microsomes (0.60–0.66 mg protein/ml), a NADPH-generating system (5 mM $MgCl_2$, 5 $\mu$M $MnCl_2$, 5 mM isocitrate, 1 mM NADP and isocitrate dehydrogenase enough to reduce 0.64 $\mu$mol NADP per minute) and the flavonoids kaempferol and quercetin respectively in a concentration of 10, 50 and 100 $\mu$mM..

Figure 2B:
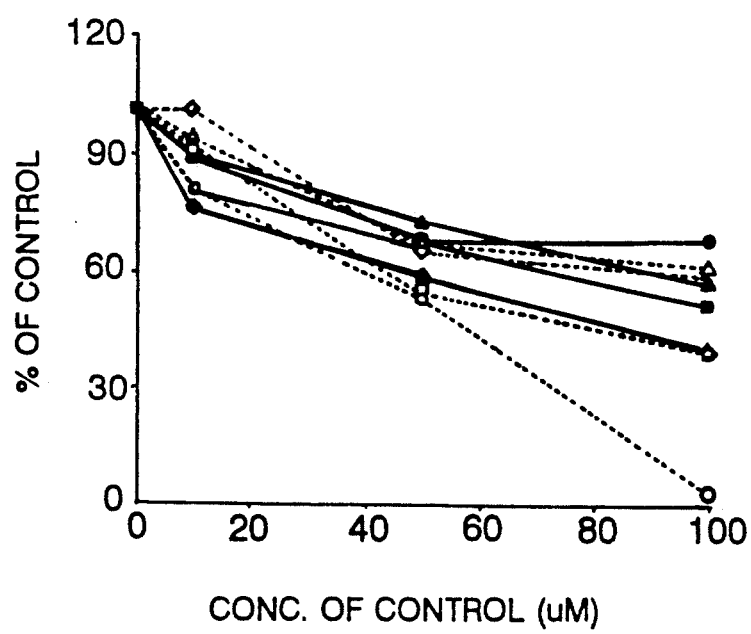

The incubation was performed at 37° C. and then terminated when adding 2 ml toluene, which denatured the proteins. The incubation time varied between 6 and 10 minutes. The felodipine was analyzed as in Example 1. The results are shown in FIG. 2. The flavonoid inhibition of felodipine metabolism did not show any sterospecificity.

EXAMPLES 3-5

The following compositions according to the present invention were prepared:

EXAMPLE 3

| | |
|---|---|
| Quercetin-glucoside (Rutin) | 100 mg |
| Felodipine | 10 mg |
| Polyoxyl stearate (Myrj ® 51) | 60 mg |
| Hydroxypropyl methylcellulose (HPMC) | 200 mg |
| Microcrystalline cellulose (Avicel) | 10 mg |
| Lactose | 85 mg |
| Ethanol | q.s |
| Sodium stearyl fumarate (SSF) | 10 mg |

Rutin, HPMC, Avicel and lactose were dry mixed in an intensive mixer.

Felodipine and Myrj were dissolved in ethanol and the solution used as granulating liquid for the dry powder mix. The moist mass was forced through a sieve and dried. After admixing SSF to the dried mass, tablets (475 mg) were compressed (11 mm) diameter, round tablets). The tablets were film coated.

EXAMPLE 4

| | |
|---|---|
| Kaempferol-glucoside | 200 mg |
| Cortison acetate | 25 mg |
| Lactose | 84 mg |
| Microcrystalline cellulose (Avicel) | 20 mg |
| Polyvinylpyrrolidone (PVP) | 7 mg |
| Water | q.s |
| Sodium stearyl fumarate | 4 mg |

Kaempferol-glucoside, cortison acetate, lactose and Avicel were dry mixed and wet granulated with a water solution of PVP. The wet mass was forced through a sieve and then dried. SSF was admixed and tablets (340 mg) were compressed using 10 mm round punches.

EXAMPLE 5

| | |
|---|---|
| Kaempferol-glucoside | 50 mg |
| Quercetin-glucoside (Rutin) | 25 mg |
| Naringenin-glucoside (Naringin) | 75 mg |
| Cyclosporin (Cyclosporin A) | 50 mg |
| Sorbitol | 100 mg |
| Ethanol | 100 mg |

| -continued | |
|---|---|
| Corn oil | 440 mg |

The solid substances were dissolved in ethanol/corn oil. The solution (840 mg) was dispensed into soft gelatin capsules. The final weight of the soft gelatin capsule was 1170 mg.

We claim:

1. A method for increasing the bioavailability of a pharmaceutical agent susceptible to oxidation by cytochrome P-450, which method comprises the step of administering to a patient in need of therapy an effective amount of said pharmaceutical agent and, simultaneously with or before or after administration of said pharmaceutical agent, administering to said patient an effective amount of a flavonoid [as defined in claim 10] of the formula I:

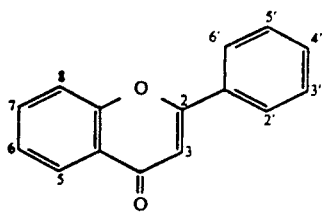

wherein one or more of the ring carbons in positions 3, 5, 7, 2', 3' and 4' are substituted by hydroxy residues, or the 4' position is optionally substituted by a methoxy residue, the flavonoid being in the form of the aglycone or glycoside, such that the concentration of the pharmaceutical agent in the serum of the patient is increased compared to the concentration when the flavonoid is not administered.

2. A method according to claim 1, wherein the pharmaceutical agent is felodipine or nifedipine.

3. A method according to claim 1, wherein two to six of the ring carbons are substituted by hydroxy residues.

4. A method according to claim 1, wherein the pharmaceutical agent is an anti-hypertensive dihydropyridine of the formula II

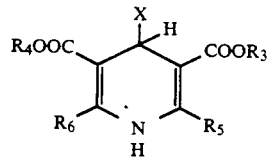

where X is an optionally substituted phenyl group, or a group

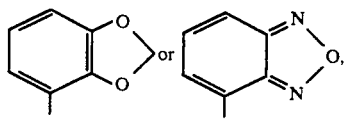

$R_4$ is a group —Y—Z, wherein Y is a straight or branched chain $C_{1-4}$ alkylene group and Z is either hydrogen, $C_{1-4}$ alkoxy or a group —$ONO_2$, $R_5$ is a straight or branched chain $C_{1-4}$ alkyl, aminoalkyl or carbamylalkyl group, or a cyano group, $R_6$ is a straight or branched chain $C_{1-4}$ alkyl group, and $R_3$ is as defined for $R_4$ or a cyclic phosphate ester, or a branched aza alkyl group wherein the nitrogen atom is at a branched point.

5. A method according to claim 1, wherein the flavonoid is guercetin-glucoside, Kaempferol-glucoside or naringenin-glucoside.

6. A method according to claim 1, wherein there is administered 1-50 mg of the pharmaceutical agent and 100-1000 mg of the flavonoid.

7. A method according to claim 1, wherein the flavonoid is contained in grape juice.

* * * * *

UNITED STATES PATENT AND TRADEMARK OFFICE
CERTIFICATE OF CORRECTION

PATENT NO. : 5,229,116
DATED : July 20, 1993
INVENTOR(S) : Boo E. Edgar et al.

It is certified that error appears in the above-identified patent and that said Letters Patent is hereby corrected as shown below:

Column 8,
Line 42, replace "grape juice" with -- grapefruit juice --.

Signed and Sealed this

Twenty-third Day of July, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 5,229,116
DATED : July 20, 1993
INVENTOR(S) : Boo E. Edgar et al.

It is certified that error appears in the above-identified patent and that said Letters Patent is hereby corrected as shown below:

Column 8,
Line 42, replace "grape juice" with -- grapefruit juice --.

Signed and Sealed this

Thirteenth Day of January, 2004

JON W. DUDAS
*Acting Director of the United States Patent and Trademark Office*